United States Patent [19]

Lundt et al.

[11] Patent Number: 5,529,576

[45] Date of Patent: Jun. 25, 1996

[54] PROSTHETIC LIMB AND ALIGNMENT ADAPTER

[75] Inventors: Judd E. Lundt, Hermosa Beach; David H. Littig, Ventura, both of Calif.

[73] Assignee: United States Manufacturing Company, Pasadena, Calif.

[21] Appl. No.: 217,047

[22] Filed: Mar. 23, 1994

[51] Int. Cl.⁶ .................................................. A61F 2/60
[52] U.S. Cl. ........................................ 623/38; 623/27
[58] Field of Search ................................ 623/38, 39, 27, 623/35, 55

[56] References Cited

U.S. PATENT DOCUMENTS

| | | | |
|---|---|---|---|
| 3,659,294 | 5/1972 | Glabiszewski | 623/38 |
| 3,663,967 | 6/1972 | Vermillion | 623/38 |
| 4,051,558 | 10/1977 | Vallotton | 623/31 |
| 4,547,913 | 10/1985 | Phillips | 623/27 |
| 4,969,911 | 11/1990 | Greene | 623/38 |
| 4,994,086 | 2/1991 | Edwards | 623/39 |
| 5,047,063 | 10/1991 | Chen | 623/38 |
| 5,116,384 | 5/1992 | Wilson et al. | 623/55 |
| 5,201,775 | 4/1993 | Arbogast et al. | 623/38 |
| 5,217,500 | 6/1993 | Phillips | 623/38 |
| 5,425,781 | 6/1995 | Allard et al. | 623/55 |

Primary Examiner—David H. Willse
Assistant Examiner—Bruce E. Snow
Attorney, Agent, or Firm—Christie, Parker & Hale

[57] ABSTRACT

A prosthetic limb and alignment adapter includes an elongated straight, flat bar that elastically flexes in fore and aft directions while being resistant to flexion in the lateral directions. A separate adjustable prosthetic link is fastened to each end of the straight, flat, flexible bar. Each prosthetic link includes a two-component, male/female adapter in which a socket having an integral bracket is affixed to an end portion of the flat bar so the axis of the socket is aligned generally with the axis of the flat, flexible bar. A cooperating angular adjustment component of the link comprises a frustopyramidal, four-sided boss divergingly projecting from a spherically convex base which slidably engages a correspondingly concave surface of the annular socket surrounding the boss. Two pairs of set screws set 90° apart in the angular socket are tightened against the sides of the frustopyramidal boss to enable its adjustment within separate swing angles in two mutually orthogonal planes defining fore and aft positioning and lateral-medial positioning of the component parts at opposite ends of the long flat flexible bar.

3 Claims, 4 Drawing Sheets

PROSTHETIC LIMB AND ALIGNMENT ADAPTER

FIELD OF THE INVENTION

This invention relates to prosthetic devices, and more particularly, to a prosthetic leg comprising a combination of prosthetic components that provides a useful combination of flexibility and adjustability for a leg prosthesis.

BACKGROUND OF THE INVENTION

Various types of leg and foot prosthetic devices are known in the art. These devices include various forms of a rigid tubular lower leg pylon attached to an energy absorbing prosthetic foot. An adjustable angular connection can be made between the bottom of the pylon and the energy absorbing foot as disclosed in U.S. Pat. No. 4,969,911 to Greene, assigned to United State Manufacturing Company, the assignee of this application.

An alternative more flexible prosthetic leg and foot comprises a long, flat bar that forms a shin portion of the lower leg prosthesis. The lower portion of the bar is curved forward to form a foot section and a separate adjustable heel section in the form of a curved bar attaches to a lower rear portion of the shin forming bar. The foot and heel portions of the prosthesis provide spring-like members that flex when pressure is applied in order to simulate a somewhat natural walking gait. Various configurations of heel sections can be added to adjust energy absorbing characteristics. During use, the heel compresses and the foot and the shin bar flex. The flexible bar is made from a carbon filament and an epoxy resin composite material that provides the flexibility. This prosthetic foot and leg combination is sold under the trademark Flex Foot and is disclosed in U.S. Pat. Nos. 4,547,913 and 4,822,363 to Phillips, assigned to Flex Foot, Inc.

A principal use of the Flex Foot device is for a lower leg prosthesis for below-knee amputations. Although its flexibility may be desirable, the Flex Foot device lacks sufficient adjustability for making alignment changes that can be critical in certain functioning of a prosthesis.

It can also be desirable to provide certain critical angular adjustments for alignment of a lower leg prosthesis for an above-knee amputation. For instance, it may be desirable to provide a flexible lower leg prosthesis for an above-knee amputation when the lower leg prosthesis is used with a prosthetic knee joint. Further, certain prosthetic devices are used with a hip disarticulation joint. In these instances, alignment with the hip disarticulation joint and sufficient flexibility of the overall prosthesis to assist in knee flexion are desirable.

The present invention provides a prosthetic limb and alignment adapter having controlled flexibility and means for adjusting the alignment of the flexible component in various selected orientations depending upon the end use of the prosthetic device. One embodiment provides a flexible lower leg prosthesis with improved adjustability for alignment purposes. Another embodiment is adaptable to above-knee amputations, and more particularly, to hip disarticulation patients by providing improved flexibility for the knee joint function, together with an adjustable means of alignment that enables the flexibility of the overall prosthetic device to be properly controlled during use.

SUMMARY OF THE INVENTION

Briefly, one embodiment of the invention comprises a prosthetic limb and alignment adapter including an elongated straight, flat bar that elastically flexes in fore and aft directions while being resistant to flexion in the lateral directions. A separate adjustable prosthetic link is fastened to each end of the straight, flat flexible bar. Each prosthetic link includes a two-component, male/female adapter in which a socket having an integral bracket is affixed to opposite end portions of the flat bar so the axis of the socket is aligned generally with the axis of the long, flat flexible bar. A cooperating angular adjustment component of the prosthetic link comprises a frustopyramidal, four-sided boss divergingly projecting from a spherically convex base which slidably engages a correspondingly concave surface of the annular socket surrounding the boss. Two pairs of set screws set 90° apart in the angular socket are tightened against the sides of the frustopyramidal boss to enable its adjustment within separate swing angles in two mutually orthogonal planes defining fore and aft positioning and lateral-medial positioning of the component parts at opposite ends of the long, flat flexible bar.

In one embodiment of the invention, the long, flat flexible bar comprises a shin member in a lower leg prosthesis in which the prosthetic links at opposite ends of the bar attach to a prosthetic foot at one end and to a prosthetic socket at the other end. The resulting combination provides good flexibility for the lower leg prosthesis, while providing angular means of adjustment at opposite ends of the shin member for proper alignment of the lower leg prosthetic device.

In another form of the invention, the long, flat flexible bar provides a thigh member for an upper leg prosthesis in which the prosthetic links at opposite ends of the thigh member attach to prosthetic components such as a socket at the upper end and a knee joint at the lower end. The lower leg portion of the prosthetic device comprises a more rigid pylon for the shin member of the resulting prosthesis. One form of this prosthetic device is particularly useful for hip disarticulation patients in which the upper end of the long, flat flexible bar that forms the thigh member of the prosthesis attaches to a hip disarticulation joint. The adjustability of the upper and lower prosthetic links provides for proper alignment of the prosthesis relative to the hip disarticulation joint, along with improved flexibility that assists in flexion of the prosthetic knee joint. The result is an improved leg prosthesis for hip disarticulation patients with improved alignment and flexibility when compared with prior leg prostheses adapted for hip disarticulation patients.

These and other aspects of the invention will be more fully understood by referring to the following detailed description and the accompanying drawings.

DETAILED DESCRIPTION

Figure 1:
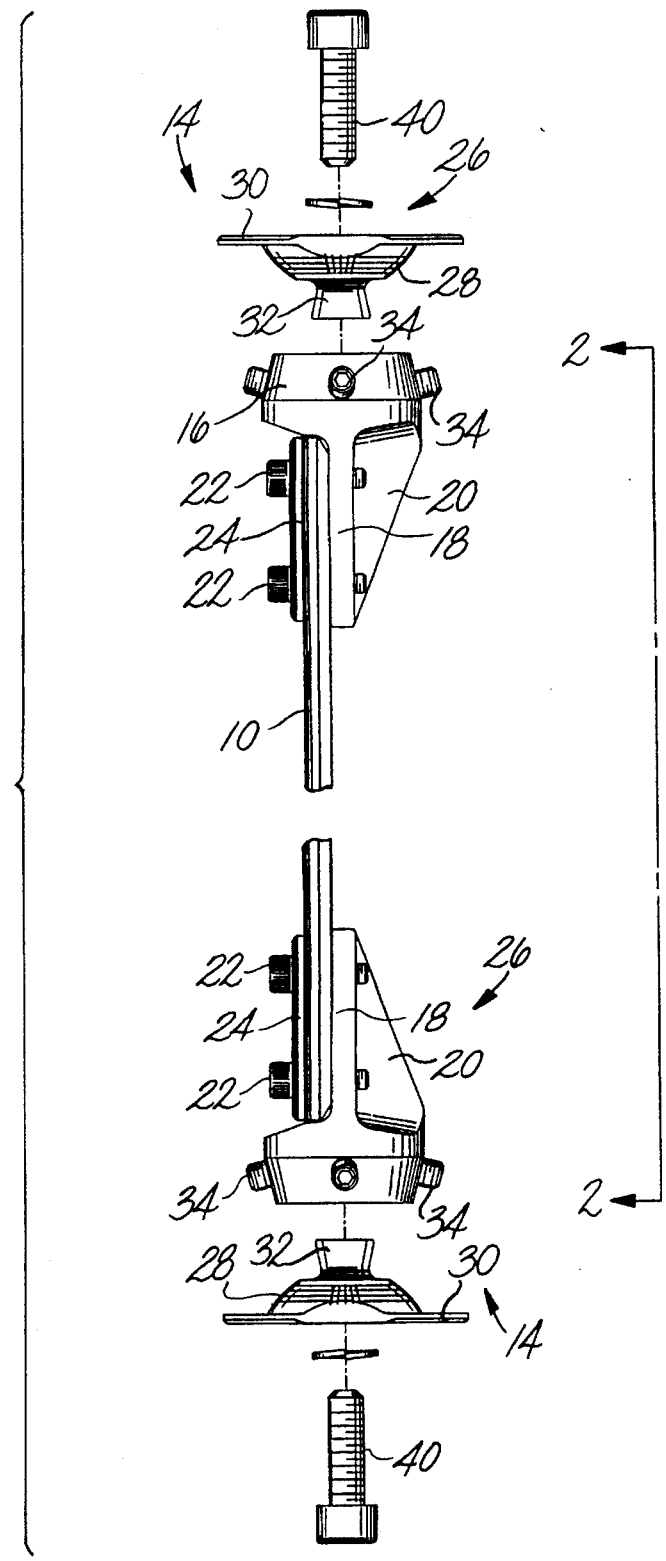
FIG. 1 is an exploded side elevational view illustrating components of a prosthetic limb and alignment adapter according to principles of this invention.
Figure 2:
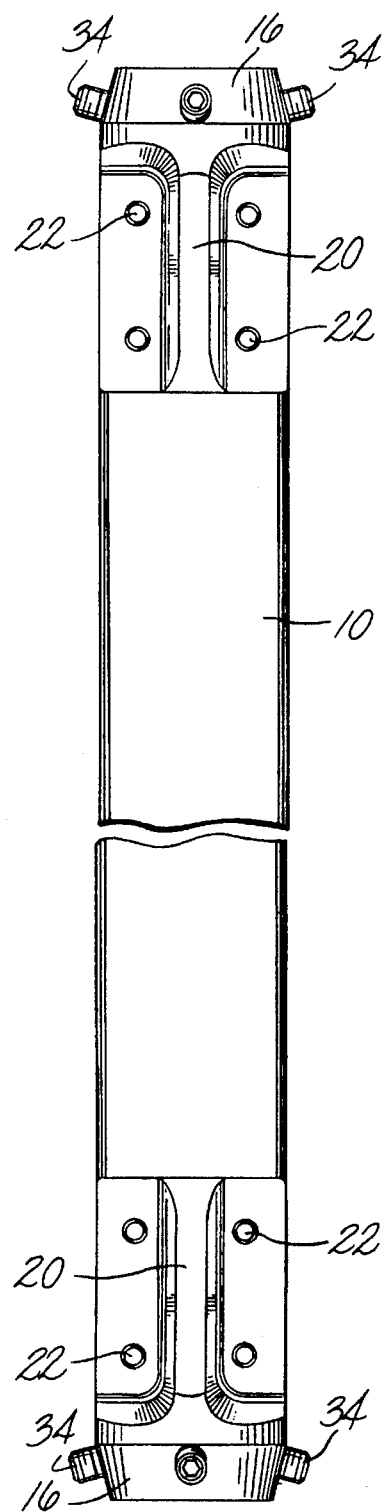
FIG. 2 is a front elevational view taken on line 2—2 of FIG. 1.

Referring to FIGS. 1 and 2, an elongated straight, flat, generally rigid bar 10 of long, narrow, generally rectangular cross section comprises the main prosthetic member of a prosthetic limb and alignment adapter. The bar is made from a high strength epoxy resin-impregnated carbon filament structure that is capable of elastically flexing in fore and aft directions perpendicular to the long cross sectional dimension of the bar, while the rigidity of the bar prevents flexing of the bar in lateral directions generally parallel to the long cross sectional dimension of the bar. A preferred structure of the bar 10 is similar to the long, straight leg portion of the prosthetic device sold under the trademark Flex Foot and described in U.S. Pat. Nos. 4,547,913 and 4,822,363 to Phillips which are incorporated herein by this reference.

A separate two-part, male/female adjustable prosthetic link 14 is affixed to each end of the long, straight flat bar 10. Each prosthetic link 14 includes male and female parts similar to the prosthetic link shown in U.S. Pat. No. 4,969,911 to Greene, which is incorporated herein by this reference. Each adjustable prosthetic link 14 is similar to the male/female prosthetic link disclosed in the '911 patent and generally includes a socket 16 having an integrally formed, vertically extending, long flat bracket 18 that overlies a face of the bar 10. The bracket includes an elongated upright generally triangularly shaped central web 20 providing a reinforcing structure for the sockets affixed to the opposite ends of the bar 10. Each socket is secured to a corresponding end of the bar by fasteners 22 extending through a flat plate 24 overlying a face of the bar opposite from the bracket 18.

Each prosthetic link further includes a male connector 26 having a spherically convex base 28 rigid with a generally flat plate 30 that provides a connector portion for the male part for connecting it to a corresponding prosthetic component. A central boss 32 of frustopyramidal configuration projects away from the spherically convex base. The frustopyramid formed by the main portion of the boss is of square cross section and has four uniform sides facing angularly upwardly and outwardly in four directions spaced apart by 90°. The four angular sides of the boss are contacted by separate set screws 34 which are carried at 90° intervals spaced apart around the bottom portion of the female socket 16. These set screws are threaded into the annular socket; they project outwardly and extend across a portion of the socket interior. The annular socket has a spherically curved concave upper ring surface having the same radius of curvature as the spherically curved base 28 of the male connector. Thus, the spherical surface of the female member can slide back and forth and can rotate on the spherical surface of the male connector. The four sides of the frustopyramidal boss extend at angles of about 14° with respect to the vertical axis through the joint, and the set screws 34 also extend along separate axes at about 14° with respect to a horizontal plane. Accordingly, each set screw can be rotated for tightening or loosening it along an axis approximately perpendicular to the confronting corresponding faces of the pyramidal boss.

In use, the male part of each connector can be inserted into the socket formed by the female part of each connector, and the set screws can be loosened or tightened and the male connector moved into various angular configurations for providing angular adjustments in a manner described in more detail in the '911 patent referred to previously. Such adjustments also are described in U.S. Pat. No. 3,659,294 to Glabiszewski, assigned to Otto Bock, which is also incorporated herein by this reference.

Thus, the cooperating male and female connectors with their two pairs of set screws set 90° apart in the annular socket can be tightened against the sides of the frustopyramidal boss to enable its adjustment within a swing angle in two mutually orthogonal planes defining fore and aft positioning, lateral-medial positioning, and combinations thereof, for the component parts of the prosthetic joints at the opposite ends of the long flat, flexible bar 10.

Figure 3:
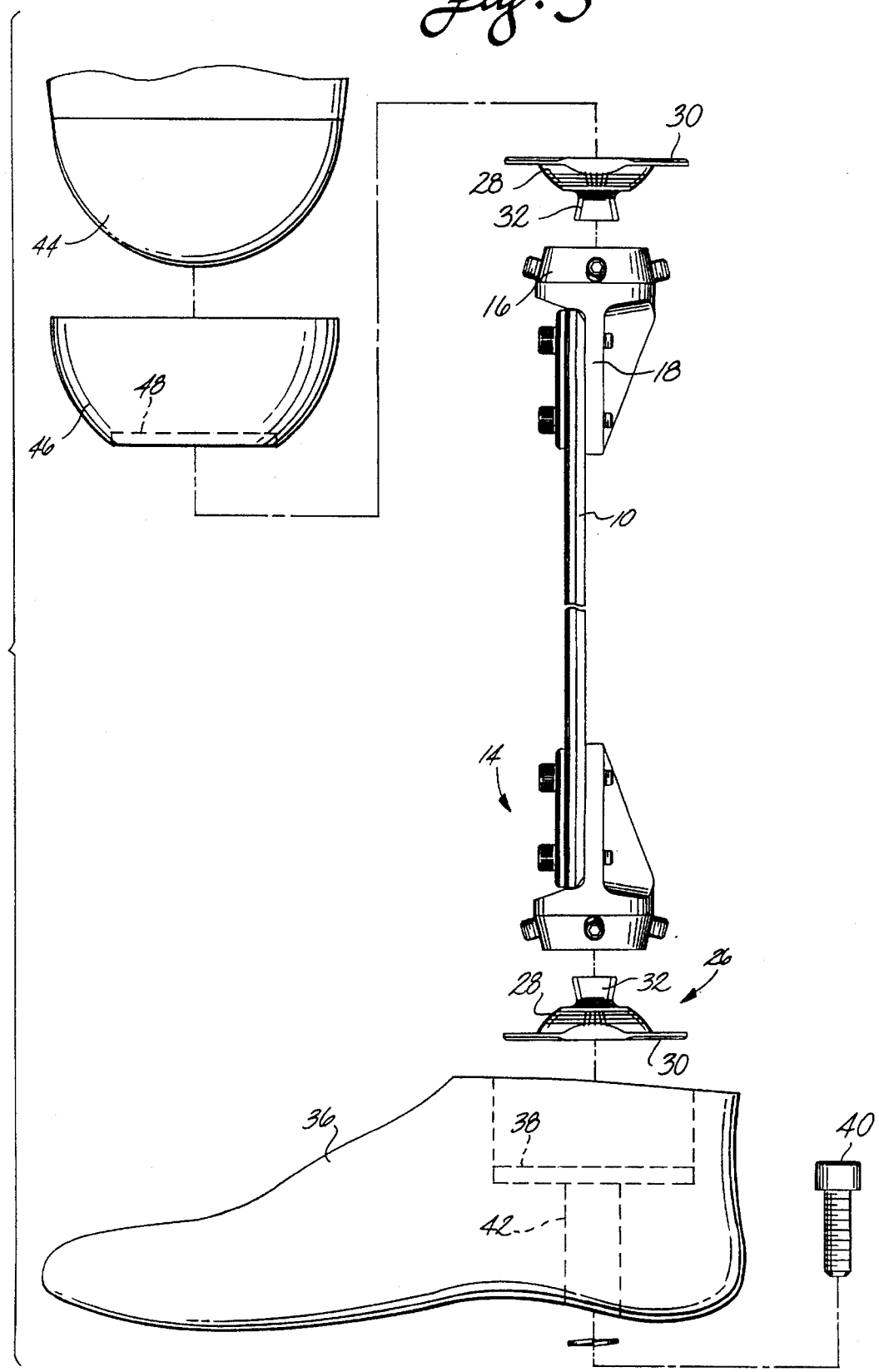
FIG. 3 is an exploded side elevational view showing the prosthetic limb and alignment adapter used in a lower leg prosthesis.

FIG. 3 illustrates one use of the prosthetic limb and alignment adapter 12. In this embodiment, the adapter is used in a lower leg prosthesis. The long, flat, flexible bar 10 forms a shin member of the lower leg prosthesis. This provides enhanced flexibility for a lower leg prosthesis when compared with the rigid tubular pylons of the prior art. In the prosthesis illustrated in FIG. 3 the long bar is of a length similar to the normal length of a patient's shin bone, and the bar flexes about an axis parallel to the long cross sectional dimension of the bar to provide bending in this area of the lower leg prosthesis. The bottom portion of the adapter is secured to an energy absorbing foot 36 of the type known in the art. The prosthetic link 14 at the bottom of the long, flat bar provides an angularly adjustable connection between the bottom of the bar and the prosthetic foot. The lower plate 30 of the male connector 26 connects to a metal plate 38 embedded in the foot. A threaded fastener 40 extends through a passage 42 in the foot below the plate 38 and threads into an internally threaded bore inside the male connector which is located inside an ankle region of the prosthetic foot. The fastener tightens against the plate to rigidly secure the male fastener of the link to the female socket portion 16. The set screws on the female connector then can be adjusted to rotate the bottom portion of the long, flat, flexible bar through swing angles in fore and aft directions and in lateral medial directions to set the position of the energy absorbing foot to a specific angular alignment with respect to the bottom of the flexible bar.

The opposite end of the lower leg prosthesis shown in FIG. 3 connects to a prosthetic socket 44, and the two-part, male/female connector secured to the top of the bar provides an angularly adjustable connection to the bottom of the socket. Although various forms of connectors can be used, one form of such a connection, as illustrated in FIG. 3, includes a cup-shaped adapter 46 which is laminated into a lower portion of the socket 44 so the adapter is rigidly affixed to the socket. A rigid plate 48 in the adapter faces downwardly toward the flanged plate 30 on the male connector. Fasteners are used to rigidly secure the flanged portion of the male connector to the flat bottom face of the plate in the socket. The male connector 26 is then engaged with the socket 16 of the female adapter and the set screws are used for loosening the two connections and allowing them to rotate through swing angles in both the fore and aft directions and the lateral and medial directions. The set screws are tightened to provide a preset angular alignment between the top of the flexible bar 10 and the prosthetic socket.

Thus, the embodiment of FIG. 3 provides a lower leg prosthesis with a flexible shin bone component and adjustable prosthetic links at both ends secured to an energy absorbing prosthetic foot at one end and a prosthetic socket at the other end in which proper angular alignment made at both ends of the flexible bar provides an improved means of control over the enhanced flexibility provided by the flexible bar component of the lower leg prosthesis.

Figure 4:
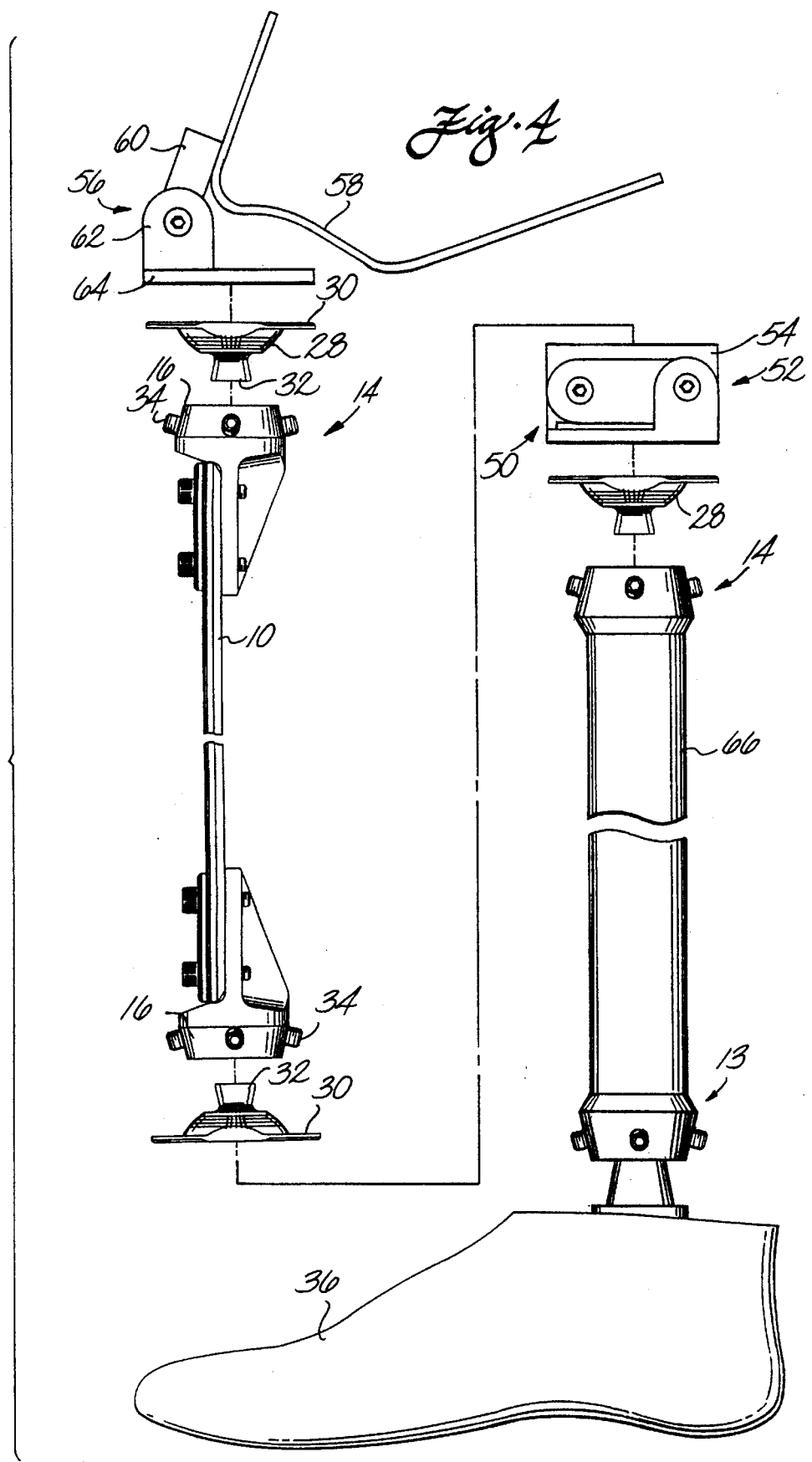
FIG. 4 is an exploded side elevational view illustrating the prosthetic limb and alignment adapter used as an upper leg component of a leg prosthesis which includes a knee joint and a hip disarticulation joint at opposite ends of the adapter.

FIG. 4 illustrates a further improved leg prosthesis in which the prosthetic limb and alignment adapter 12 forms a thigh portion of a prosthetic leg 50. In this embodiment, the leg prosthesis is a type which is used for hip disarticulations. The upper leg portion or thigh portion of the prosthesis is formed by the long, flat flexible bar 10 which has a length similar to the normal length of the patient's thigh. This provides good flexibility in the thigh region of the prosthesis in fore and aft directions while resisting flexing in the sideways directions.

The lower end of the flexible bar 10 is secured to the top portion of a prosthetic knee joint 52 through the prosthetic link 14 carried at the end of the long flat flexible bar 10. This knee joint can be various types of prosthetic knee joints such as the knee joint Product No. 15026 of United States Manufacturing Company. Other knee joints that can be used with this prosthesis include the Kolman Safety Knee Module No. 128-005, U.S. Safety Knee Module No. 128-006, and U.S. Constant Friction Knee Module No. 128-008 of United States Manufacturing Company. These knee joints generally include a flat plate 54 at the upper end that connects to the flat plate 30 of the male connector 26. The socket portion of the female connector 16 engages the frustoconical pyramid 32 of the male connector, and the set screws 34 are used to adjust the swing angles in the fore and aft directions and in the lateral-medial directions, or combinations thereof, to provide a set angular alignment between the top of the knee joint and the bottom of the flexible bar 10.

The upper end of the flat, flexible bar 10 fastens to a lower portion of a hip disarticulation joint 56. This hip joint can be in various forms such as the modular hip disarticulation joint No. P01-200 of United States Manufacturing Company. Alternatively, the disarticulation joint 56 can be the modular hip joint No. 006 7E5 of Otto Bock. The illustrated hip joint includes a socket attachment plate 58, a hip joint assembly 60 and a lower hip bracket 62 which includes a bottom plate 64 that overlies and fastens to the flat plate 30 on the male connector 26 which connects to the female socket member 16 affixed to the upper end of the long, flat, flexible bar 10. The hip disarticulation joint 56 is secured to the lower portion of a prosthetic socket (not shown) and attached to the socket so as to prevent any relative rotation between the socket and the disarticulation joint. Similarly, the flat plate 30 of the male connector is affixed to the bottom of the hip disarticulation joint to prevent any relative rotation between the two. The connection between the hip disarticulation joint and the adjustable prosthetic link provides for a precise means of adjusting swing angles in both fore and aft directions and the sideways directions, as well as combinations thereof, to provide a critical means of control over the alignment between the hip joint and the knee joint. The alignment at the pelvis is particularly critical, and the prosthetic leg of FIG. 4 provides a means for moving the knee joint forward while providing the necessary alignment. Insofar as hip disarticulations are concerned, the flexible bar aids in knee flexion not available with a standard fixed rigid pylon. For the lower leg portion of the prosthesis it is desirable, however, to use the rigid fixed tubular pylon 66 because the use of a flexible bar similar to the bar 10 in this area would, under normal circumstances, produce too much flexibility for the overall prosthesis. The opposite ends of the pylon 66 are secured to the bottom of the knee joint and the top of the prosthetic foot by prosthetic links similar to those described previously.

Thus, the embodiment of FIG. 4 provides a leg prosthesis for hip disarticulations that produces enhanced flexibility in the thigh region while aligning the knee joint forward at a desired location in alignment with the prosthesis and while enhancing flexibility of the knee joint.

A further application of the invention is for a lower leg prosthesis in which the flexible bar 10 is secured to a prosthetic knee joint at its top and a prosthetic foot at the bottom. The angularly adjustable prosthetic links 14 are used for fastening the ends of the bar to the knee joint and the foot.

What is claimed is:

1. A prosthetic limb and alignment adapter for use in an energy-storing upper leg prosthesis, comprising a hip disarticulation joint; a prosthetic knee joint; and an adjustable upper leg member secured between the hip disarticulation joint and the prosthetic knee joint, the adjustable upper leg member comprising an elongated, thin, flat, generally straight bar of generally long, narrow cross-section extending for a length similar to a thigh bone of a patient, the elongated bar having flexibility in a direction generally perpendicular to the narrow cross-sectional dimension of the bar while being resistant to flexion in a direction generally parallel to the long cross-sectional dimension of the bar so that the bar when used as a thigh bone component of a leg prosthesis can flex in fore and aft directions while being resistant to flexion in lateral-medial directions, and a separate two-part angularly adjustable prosthetic link secured to each end of the bar, each prosthetic link comprising a male attachment member and a cooperating female socket member having adjustable set screws engaging the male attachment member to provide swing angular rotational adjustment in the fore and aft directions and in the lateral and medial directions or combinations thereof, each prosthetic link having one of its components rigidly affixed to the end of the bar with the cooperating component attached to the hip disarticulation joint and to the prosthetic knee joint, so that the bar provides fore and aft plane flexion joint while providing a means of angular adjustment and alignment with respect to the hip disarticulation joint and the prosthetic knee joint.

2. Apparatus according to claim 1 in which the male attachment member of each prosthetic link is affixed to the hip disarticulation joint and to the prosthetic knee joint, and the female socket members are affixed to the opposite ends of the bar.

3. Apparatus according to claim 1 and further including a lower leg prosthesis secured to a lower portion of the prosthetic knee joint and comprising a prosthetic foot, a lower leg pylon, and an adjustable two-part prosthetic link adjustable in fore and aft directions and adjustable in lateral and medial directions, secured to the ends of the pylon and to the prosthetic foot and prosthetic knee joint, respectively.

* * * * *